US00PP25737P3

(12) United States Plant Patent
Egger

(10) Patent No.: US PP25,737 P3
(45) Date of Patent: Jul. 21, 2015

(54) ×*HEUCHERELLA* PLANT NAMED 'FIRE FROST'

(50) Latin Name: ×*Heucherella* hybrid
Varietal Denomination: Fire Frost

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 186 days.

(21) Appl. No.: 13/987,670

(22) Filed: Aug. 20, 2013

(65) Prior Publication Data

US 2015/0059038 P1 Feb. 26, 2015

(51) Int. Cl.
*A01H 5/12* (2006.01)

(52) U.S. Cl.
USPC ..... Plt./441

(58) Field of Classification Search
USPC ..... Plt./441
See application file for complete search history.

*Primary Examiner* — June Hwu

(74) *Attorney, Agent, or Firm* — Klarquist Sparkman, LLP

(57) ABSTRACT

A new and distinct ×*Heucherella* plant substantially as shown and described, characterized by lime green to yellow green leaves with red to dark brown marks on the main veins and a light white veil, large, shallowly lobed leaves, a medium large semi-trailing habit, and excellent vigor.

1 Drawing Sheet

Botanical denomination: ×*Heucherella* hybrid.
Variety designation: 'Fire Frost'.

BACKGROUND OF THE INVENTION

The present invention relates to a new and distinct cultivar of ×*Heucherella* and given the cultivar name of 'Fire Frost'. ×*Heucherella* is in the family Saxifragaceae. ×*Heucherella* 'Fire Frost' originated from a controlled cross between a proprietary unreleased seedlings *Heuchera* V4, as the seed parent, and *Tiarella* massed proprietary trailing seedlings, as the pollen parent.

Compared to the seed parent *Heuchera* V4, the new cultivar has smaller leaves with gold foliage than tan and a white veil and dark red along main veins at the leaf base rather than no veil and no red markings.

Compared to the pollen parent, the *Tiarella* seedlings, the new cultivar has larger leaves that are gold and broad rather than green and lobed and have a white veil rather than no veil.

Compared to *Heuchera* 'Delta Dawn' U.S. Plant Pat. No. 23,545, the new cultivar has leaves that are lighter in color and has markings that follow the veins and are dark burgundy rather a round center pattern that is red. The new cultivar has a white veil and *Heuchera* 'Delta Dawn' does not.

Compared to ×*Heucherella* 'Alabama Sunrise' U.S. Plant Pat. No. 19,611, the new cultivar is shallowly rather than deeply lobed.

This new ×*Heucherella* is unique in having the following characteristics:

1. lime green to yellow green leaves with red to dark brown marks on the main veins and a light white veil,
2. large, shallowly lobed leaves,
3. a medium large semi-trailing habit, and
4. excellent vigor.

This new cultivar has been reproduced only by asexual propagation (division, cuttings, and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a 4 month old greenhouse grown ×*Heucherella* 'Fire Frost' in a gallon container grown inside in an unheated greenhouse in April in Canby, Oreg.

FIG. 2 shows a 10 month old plant showing the late summer to winter color in Canby, Oreg.

DETAILED PLANT DESCRIPTION

The following is a detailed description of the new ×*Heucherella* cultivar based on observations of eighteen-month-old specimens growing in the garden in part shade in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on *The Royal Horticultural Society Colour Chart*, $5^{th}$ edition.

Plant:

*Form.*—Basal rosette and trailing, herbaceous perennial.
*Hardiness.*—USDA Zone 4 to 9.
*Size.*—27 cm tall from top of the foliage to the ground and 57 cm wide.
*Habit.*—Low clumping and trailing.
*Vigor.*—Excellent.
*Roots.*—Fibrous, freely branching, fine, and white in color.

Stem:

*Size.*—Grows to 6 mm wide and 18 cm long.

*Surface texture.*—Glandular pubescent.

*Internode length.*—1 cm to 4.5 cm.

*Stem color.*—Yellow Green 145C in shade to tinted Greyed Purple 187B in light.

Leaf:

*Type.*—Simple.

*Arrangement.*—Rosette and alternate.

*Shape.*—Broadly ovate to orbicular.

*Lobing/division.*—5 to 7 shallow palmate lobes.

*Venation.*—Palmate, Yellow Green 145A.

*Margins.*—Crenate.

*Apex.*—Mucronulate.

*Base.*—Cordate, lobes usually overlapping slightly.

*Blade size.*—Grows to 11 cm long and 11 cm wide.

*Surface texture.*—Glandular both surfaces.

*Petiole description.*—Grows to 17 cm long and 3 mm wide, glandular hairs, Yellow Green 145B in low light, tinted Greyed Purple 187B in higher light.

*Leaf color.*—Topside and bottom sides spring Yellow Green 145A; topside summer Yellow Green 146C with pattern along the main veins Greyed Purple 184A, bottom side Yellow Green 146D with pattern along the main veins tinted Greyed Purple N186D; topside late summer to winter same as summer except for the addition of a light white veil over the inside ¾ of the blade.

Inflorescence:

*Size.*—Grows to 3 cm wide and 17 cm long.

*Type.*—Raceme.

*Number of flowers per raceme.*—About 80.

*Number of racemes.*—About 10.

*Peduncle.*—Grows to 37 cm tall, 2 mm wide at base, glandular hairs, Yellow Green 145C.

*Pedicel.*—Grows to 5 mm long, with glandular hairs, Yellow Green 145C.

*Bloom period.*—Mid-summer in Canby, Oreg.

Flower bud:

*Size.*—2 mm wide and 3 mm long.

*Description.*—Glandular puberulent, ovoid.

*Color.*—White N155B.

Flower:

*Type.*—Perfect.

*Shape.*—Campanulate.

*Size.*—6 mm deep and 4 mm wide.

*Petal description.*—5 in number, linear to narrowly lanceolate, 6 mm long and less than 1 mm wide, tip acuminate, base attenuate, margin entire, glabrous and White NN155B on both sides.

*Calyx description.*—3.5 mm deep and 2.5 mm wide, with 5 lobes, divided ½ way to the base, campanulate, glandular hairs outside, glabrous inside, tip acute, margin entire, White NN155B.

*Stamen description.*—10 in number, filaments 3 mm long, White NN155A, anthers sterile, less than 1 mm, Yellow Orange 17A.

*Pistil description.*—One central two beaked pistil, 4 mm long, White NN155A.

*Fragrance.*—None.

*Lastingness.*—Each raceme blooms for about 2 weeks on the plant.

*Flower attitude.*—Semi-upwards.

*Flowering stem attitude.*—Upright.

Fruit and seed: None.

Disease and pest tolerance: The new cultivar is typical to the genus. No known resistances to pests or diseases. No problems have been found in Canby, Oreg.

I claim:

1. A new and distinct ×*Heucherella* plant as herein illustrated and described.

* * * * *

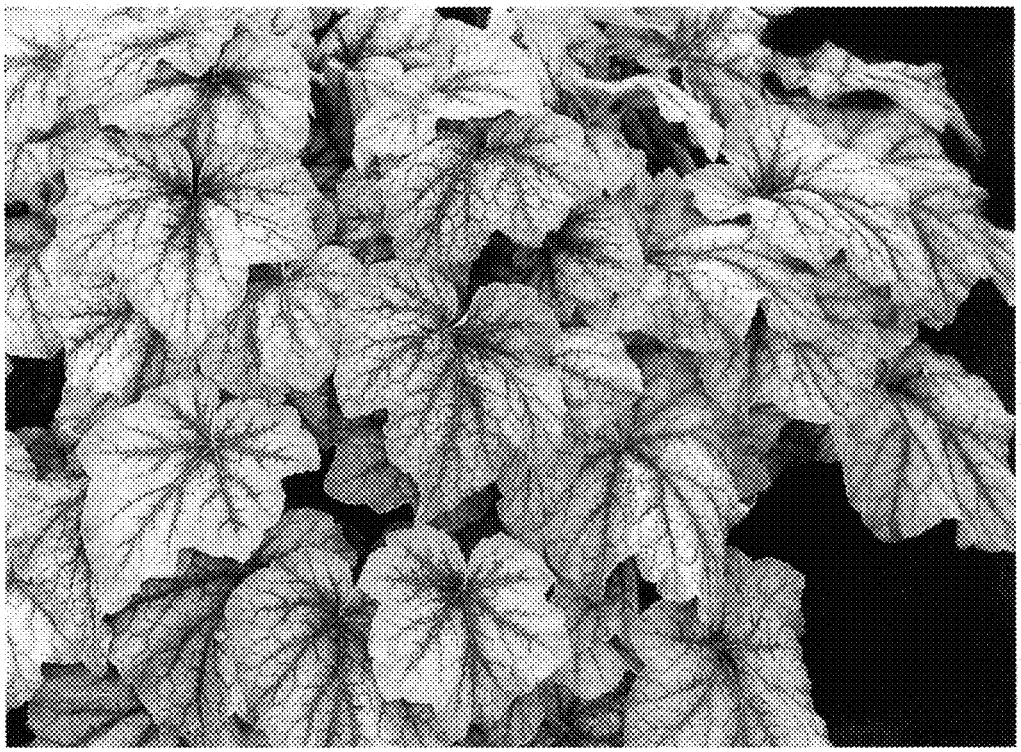

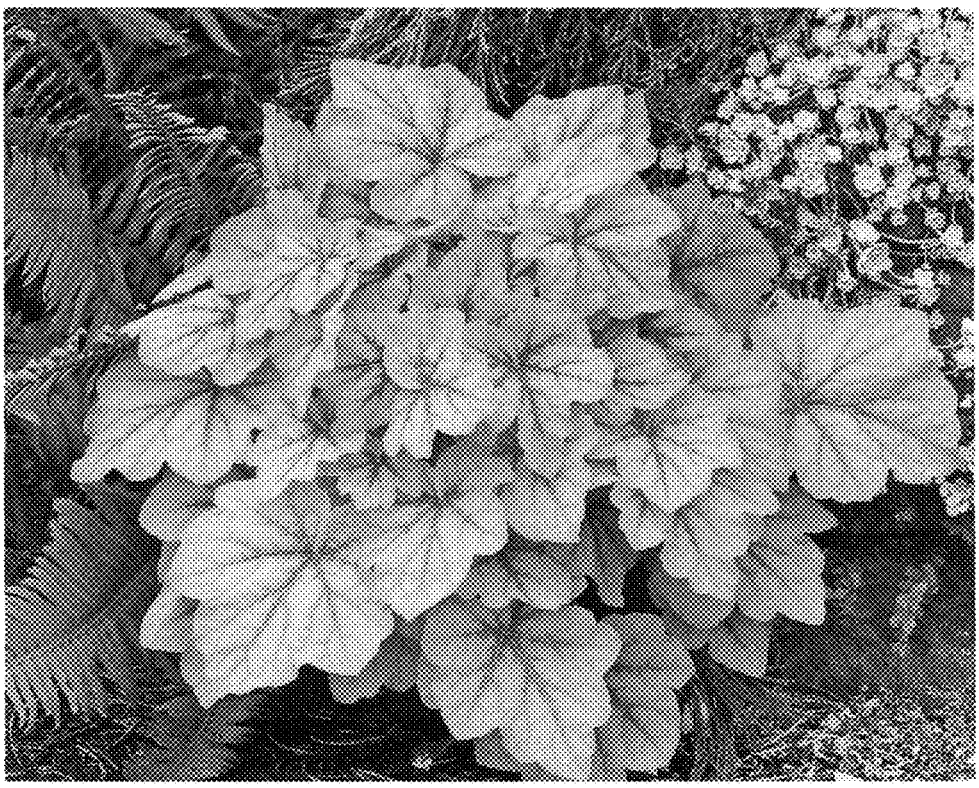
FIG. 1 above, FIG. 2 below